US010426891B2

(12) United States Patent
Johansen

(10) Patent No.: US 10,426,891 B2
(45) Date of Patent: Oct. 1, 2019

(54) DISPOSABLE CASSETTE FOR STORING AND DELIVERING A MEDICAL DRUG

(71) Applicant: Medicom Innovation Partner A/S, Struer (DK)

(72) Inventor: Esben W. Johansen, Struer (DK)

(73) Assignee: Medicom Innovation Partner A/S, Struer (DK)

( * ) Notice: Subject to any disclaimer, the term of this patent is extended or adjusted under 35 U.S.C. 154(b) by 128 days.

(21) Appl. No.: 15/305,802

(22) PCT Filed: Apr. 17, 2015

(86) PCT No.: PCT/EP2015/058416
§ 371 (c)(1),
(2) Date: Oct. 21, 2016

(87) PCT Pub. No.: WO2015/165757
PCT Pub. Date: Nov. 5, 2015

(65) Prior Publication Data
US 2017/0043091 A1 Feb. 16, 2017

(30) Foreign Application Priority Data

Apr. 29, 2014 (DK) .................................. 2014 70248

(51) Int. Cl.
*A61M 5/20* (2006.01)
*A61M 5/00* (2006.01)
(Continued)

(52) U.S. Cl.
CPC .............. *A61M 5/20* (2013.01); *A61M 5/007* (2013.01); *A61M 5/19* (2013.01); *A61M 5/24* (2013.01);
(Continued)

(58) Field of Classification Search
CPC ............ A61M 5/20; A61M 5/19; A61M 5/24; A61M 5/3146; A61M 5/28; A61M 5/007;
(Continued)

(56) References Cited

U.S. PATENT DOCUMENTS

| 4,820,286 A | 4/1989 | van der Wal |
| 5,034,003 A | 7/1991 | Denance |

(Continued)

FOREIGN PATENT DOCUMENTS

| CN | 87103434 A | 11/1987 |
| CN | 1886165 A | 12/2006 |

(Continued)

OTHER PUBLICATIONS

International Search Report PCT/ISA/210 for International Application No. PCT/EP2015/058416 dated Jun. 29, 2015.
(Continued)

*Primary Examiner* — Theodore J Stigell
(74) *Attorney, Agent, or Firm* — Harness, Dickey & Pierce, P.L.C.

(57) ABSTRACT

A disposable cassette (1) for storing and delivering a medical drug, the cassette (1) comprising a cartridge (7) containing the medical drug, a waste reservoir (8) arranged to receive waste liquid and/or gas, an injection needle (9)arranged to deliver the medical drug, and a valve block (10) being movable between a first position and a second position. The first position establishes a fluid passage between the cartridge (7) and the waste reservoir (8), while preventing fluid flow from the cartridge (7) to the injection needle (9), and the second position establishes a fluid passage between the cartridge (7) and the injection needle (9), while preventing fluid flow from the cartridge (7) to the waste reservoir (8). The cartridge (7), the waste reservoir (8), the valve block (10) and at least part of the injection needle (9)
(Continued)

are arranged inside a cassette housing (2), and the valve block (10) is operable to be moved between the first position and the second position without a user operating the cassette (1) coming into direct contact with parts arranged inside the cassette housing (2).

15 Claims, 13 Drawing Sheets

(51) Int. Cl.
*A61M 5/19* (2006.01)
*A61M 5/24* (2006.01)
*A61M 5/28* (2006.01)
*A61M 5/31* (2006.01)
*A61M 39/22* (2006.01)

(52) U.S. Cl.
CPC .............. *A61M 5/28* (2013.01); *A61M 5/284* (2013.01); *A61M 5/3146* (2013.01); *A61M 39/223* (2013.01); *A61M 2005/3128* (2013.01); *A61M 2202/049* (2013.01); *A61M 2205/12* (2013.01); *A61M 2205/128* (2013.01)

(58) Field of Classification Search
CPC .............. A61M 5/284; A61M 2205/12; A61M 2205/18; A61M 39/223
See application file for complete search history.

(56) References Cited

U.S. PATENT DOCUMENTS

| | | | |
|---|---|---|---|
| 5,289,858 | A | 3/1994 | Grabenkort |
| 2003/0004463 | A1* | 1/2003 | Reilly ................ A61K 51/1282 604/124 |
| 2003/0216609 | A1 | 11/2003 | Dell et al. |
| 2004/0254525 | A1 | 12/2004 | Uber et al. |
| 2004/0260143 | A1 | 12/2004 | Reilly et al. |
| 2005/0085682 | A1 | 4/2005 | Sasaki et al. |
| 2005/0238576 | A1 | 10/2005 | Dell et al. |
| 2010/0185040 | A1 | 7/2010 | Uber, III et al. |
| 2010/0286609 | A1 | 11/2010 | Mahurkar |
| 2013/0253254 | A1 | 9/2013 | Uber, III et al. |

FOREIGN PATENT DOCUMENTS

| | | |
|---|---|---|
| CN | 101175519 A | 5/2008 |
| CN | 101370534 A | 2/2009 |
| CN | 101879342 A | 11/2010 |
| CN | 103071202 A | 5/2013 |
| CN | 103153360 A | 6/2013 |
| CN | 103338799 A | 10/2013 |
| EP | 1938771 A1 | 7/2008 |
| EP | 1938772 A1 | 7/2008 |
| JP | H06-233819 A | 8/1994 |
| JP | 2002078799 A | 3/2002 |
| JP | 2012-509717 A | 4/2012 |
| WO | WO-93/12002 A1 | 6/1993 |
| WO | WO-2004/091688 A2 | 10/2004 |
| WO | WO-2005/051465 A1 | 6/2005 |
| WO | WO-2006/060688 A2 | 6/2006 |
| WO | WO-2007/070570 A2 | 6/2007 |
| WO | WO-2006/124819 A1 | 11/2008 |
| WO | WO-2010/068415 A1 | 6/2010 |
| WO | WO-2012/030316 A1 | 3/2012 |
| WO | WO-2012/072569 A1 | 6/2012 |

OTHER PUBLICATIONS

Written Opinion of the International Searching Authority PCT/ISA/237 for International Application No. PCT/EP2015/058416 dated Jun. 29, 2015.
International Preliminary Report on Patentability PCT/IPEA/416 for International Application No. PCT/EP2015/058416 dated Jun. 23, 2016.
Chinese Office Action dated Feb. 15, 2019 for corresponding Chinese Application No. 201580021521.8.
Japanese Office Action dated Mar. 5, 2019 for corresponding Japanese Application No. 2016-563196.

\* cited by examiner

DISPOSABLE CASSETTE FOR STORING AND DELIVERING A MEDICAL DRUG

CROSS-REFERENCE TO RELATED APPLICATIONS

This application is the U.S. National Phase application of PCT Application No. PCT/EP2015/058416 filed on Apr. 17, 2015 which claims priority to Danish Patent Application No. PA2014 70248 filed on Apr. 29, 2014, the entire contents of which are incorporated herein by reference.

FIELD OF THE INVENTION

The present invention relates to a disposable cassette for storing and delivering a medical drug. The cassette of the invention allows the medical drug to be delivered, and possibly mixed, without a user operating the cassette coming into contact with the drug. Thereby the cassette of the invention is safe to handle.

BACKGROUND OF THE INVENTION

Some kinds of injectable medical drug are highly toxic, or it may for other reasons be undesirable that patients or health care personnel come into contact with the medical drug or fumes originating from the medical drug, except for the actual administration of the drug. One example of such kinds of drugs are those used for oncology treatment. Another example is drugs which are stored in dry form, e.g. lyophilised drugs, and which need to be reconstituted by mixing the dry drug with a liquid diluent prior to administration of the drug.

Drugs which are stored in dry form and need to be reconstituted prior to administration are sometimes stored and administered by means of a dual chamber syringe. In such syringes the dry drug and the diluent are stored in separate cavities. When it is desirable to deliver the drug, the syringe is initially operated in order to bring the dry drug and the diluent into contact, thereby causing reconstitution of the drug. Subsequently, the syringe is operated in order to cause the reconstituted drug to be delivered from the syringe. Following the reconstitution of the drug, a relatively large amount of air or gas is sometimes present in the syringe. Such air or gas must be removed from the syringe before administration of the drug, in particular in the case that the drug is to be injected. To this end a so-called air shot is performed. However, in the case that the drug produces fumes which are toxic or the like, it is important that the air shot is contained in order to ensure that the fumes, and possible liquid waste, are disposed of in a controlled and responsible manner.

In some prior art injection systems, health care personnel must manually manipulate various parts of the injection system, in order to cause the drug to be injected, and possibly in order to cause reconstitution of the drug and/or air shots. This introduces the risk that the health care personnel and/or the patient come into contact with the drug, and/or that the drug and/or fumes originating from the drug are spilled.

DESCRIPTION OF THE INVENTION

It is an object of embodiments of the invention to provide a cassette for storing and delivering a medical drug, in which it is prevented that health care personnel get into direct contact with the drug.

It is a further object of embodiments of the invention to provide a cassette for storing and delivering a medical drug, in which it is ensured that spilled drug and/or fumes originating from the drug are safely contained.

According to a first aspect the invention provides a disposable cassette for storing and delivering a medical drug, the cassette comprising:

a cartridge containing the medical drug, a waste reservoir arranged to receive waste liquid and/or gas, an injection needle or an injection needle mounting interface for mounting an injection needle arranged to deliver the medical drug, and a valve block being movable between a first position and a second position, the first position establishing a fluid passage between the cartridge and the waste reservoir, while preventing fluid flow from the cartridge to the injection needle or the injection needle mounting interface, and the second position establishing a fluid passage between the cartridge and the injection needle or the injection needle interface, while preventing fluid flow from the cartridge to the waste reservoir, wherein the cartridge, the waste reservoir, the valve block and at least part of the injection needle or the injection needle mounting interface are arranged inside a cassette housing, and wherein the valve block is operable to be moved between the first position and the second position without a user operating the cassette coming into direct contact with parts arranged inside the cassette housing.

The present invention relates to a disposable cassette for storing and delivering a medical drug. Thus, the cassette is manufactured and sold with the medical drug contained therein, and the medical drug is thereby stored inside the cassette until it is time to deliver the medical drug to a patient. Then the medical drug contained in the cassette is delivered to the patient, and afterwards the cassette is disposed of.

The disposable cassette comprises a cartridge, a waste reservoir, an injection needle or an injection needle mounting interface, and a valve block, which are all at least partly arranged inside a cassette housing. In the present context the term 'housing' should be interpreted to mean a substantially closed part which defines a cavity in an interior part thereof, and which substantially encloses a number of parts arranged in the cavity. Thus, the cassette housing encloses the cartridge, the waste reservoir, the valve block and at least part of the injection needle or the injection needle mounting interface, and a user operating the cartridge is not readily capable of coming into contact with these parts, except for the injection needle which may be brought into a position where it protrudes from the cassette housing in order to allow the medical drug to be delivered by means of the injection needle.

The cartridge contains the medical drug which is stored and delivered by means of the cassette.

The waste reservoir is arranged to receive waste liquid and/or gas. In the present context the terms 'waste liquid' and 'waste gas' should be interpreted to mean liquid or gas which is not delivered to a patient, and which must be disposed of. This could, e.g., include gas and/or liquid resulting from an air shot performed prior to delivery of the drug. Such waste liquid and/or gas may be toxic or otherwise hazardous, and it may therefore be necessary that the waste liquid and/or gas is disposed of in a controlled and safe manner. It is therefore an advantage that the waste reservoir is arranged inside the cassette housing, because thereby it is prevented that waste liquid and/or gas leaves the cassette housing, and that the waste liquid and/or gas comes into contact with a user operating the cassette. Furthermore, the cassette, including the waste liquid and/or gas contained in the waste reservoir, can be transported in a safe manner to a site where safe disposal of the cassette can be performed, after use of the cassette.

The injection needle is arranged to deliver the medical drug. Thus, when the cassette is operated to deliver the medical drug, the injection needle is arranged at an injection site, and the drug is delivered to the injection site, via the injection needle. The injection needle may be fixedly mounted in the cassette. As an alternative, the injection needle may be detachable. In this case, the cassette may be stored without the injection needle, and the injection needle may be mounted at a connector or needle mounting interface of the cassette when it is desired to operate the cassette to deliver the medical drug contained therein. It should be noted that the injection needle could be in the form of an infusion needle which is mounted at a needle mounting interface via a tube. In this case the infusion needle may be positioned at some distance from the cassette housing, but will be fluidly connected thereto via the tube. In some cases such tubing connections may end in another interface connection apart from a needle for injection of drug product into the patient tissue, e.g. connection to an implantable catheter for direct vein access, such as a Port-a-Cath (e.g. manufactured by Smiths Medical) system, which then may replace the use of a dedicated needle.

The valve block is movable between a first position and a second position. The first position establishes a fluid passage between the cartridge and the waste reservoir, while preventing a fluid flow from the cartridge to the injection needle. Thus, when the valve block is in the first position, waste liquid and/or gas can be transferred from the cartridge to the waste reservoir, via the established fluid passage. Simultaneously, it is prevented that any fluid or gas leaves the cassette via the injection needle, since fluid flow from the cartridge to the injection needle is prevented. Accordingly, the valve block may advantageously be in the first position during an air shot.

The second position establishes a fluid passage between the cartridge and the injection needle, while preventing fluid flow from the cartridge to the waste reservoir. Thus, when the valve block is in the second position, medical drug can be delivered from the cartridge, via the established fluid passage and the injection needle. Simultaneously it is ensured that the entire dose of medical drug is delivered via the injection needle, since fluid flow from the cartridge to the waste reservoir is prevented. Accordingly, the valve block may advantageously be in the second position during delivery or injection of the medical drug.

The valve block is operable to be moved between the first position and the second position without a user operating the cassette coming into direct contact with the parts arranged inside the cassette housing. Thus, the user operating the cassette will not have to physically and directly handle the parts arranged inside the cassette housing. For instance, the user will not need to manually move the valve block between the first and second position. Instead, the valve block may, e.g., be operated indirectly, e.g. by means of a manipulating mechanism arranged outside the cassette housing. As an alternative, it may be operated automatically when other parts arranged inside the cassette housing are moved during operation of the cassette. As another alternative, the valve block may be operated in a contact-less manner, e.g. by means of a movable magnet arranged outside the cassette housing cooperating with a manipulator of a magnetisable material arranged inside the cassette housing, or by wirelessly transferring operating signals into the cassette housing. The fact that the user does not come into direct contact with the parts arranged inside the cassette housing considerably reduces the risk of the user coming into direct contact with the medical drug being stored and delivered by means of the cassette, or fumes hereof.

For instance, the valve block may be operable to be moved between the first position and the second position without the need to open or enter the cassette housing. According to this embodiment, the user operating the cassette does not need to open or access the cassette housing in order to manipulate the valve block in such a manner that it is moved between the first and the second positions.

The disposable cassette may further comprise a manipulating mechanism arranged on an exterior part of the cassette housing, the manipulating mechanism being connected to the valve block in such a manner that operating the manipulating mechanism causes the valve block to be moved between the first position and the second position. According to this embodiment, the valve block can be operated by manipulating the manipulating mechanism. Since the manipulating mechanism is arranged on an exterior part of the cassette housing, the valve block is thereby operable without the user operating the cassette coming into direct contact with the parts arranged inside the cassette housing, and without having to open or enter the cassette housing.

The valve block may be arranged to be automatically moved between the first position and the second position during operation of the cassette in order to cause medical drug to be delivered. According to this embodiment, the valve block can be operated without the user operating the cassette actively and separately operating the valve block. Instead the valve block is operated concurrently with the operation of the cassette, and as an automatic consequence of the operation of the cassette in order to cause medical drug to be delivered. This also efficiently ensures that the user operating the cassette does not come into contact with parts arranged inside the cassette housing.

In the present context the term 'operation of the cassette in order to cause medical drug to be delivered' should be interpreted in a broad manner, in the sense that it should not be restricted to covering only the actual delivery or injection of the medical drug. Instead it should be interpreted to cover an entire process taking place when it is desired to deliver the medical drug stored in the cassette. Apart from the actual delivery or injection of the drug, such a process may, e.g., include preparing the cassette for injection, breaking of seals of the cassette, reconstitution of the medical drug, moving the injection needle to an injection position, etc.

According to this embodiment, the movement of the valve block between the first position and the second position may be caused by the movement of other parts arranged inside the cassette housing, where the movements of the other parts are performed as a part of the delivery process, possibly including the steps mentioned above. Thereby it is further ensured that the movement of the valve block between the first and second positions is synchronized with the delivery process.

The valve block may comprise a compressible spring, and the valve block may be moved from the first position to the second position when energy stored in the spring is released. According to this embodiment, energy is stored in the compressible spring during manufacture of the cassette. Thus, during storage of the cassette, the compressible spring is in a loaded or energized state, and the valve block is preferably in the first position. At a suitable point in time during the delivery process, the energy stored in the spring is released, thereby causing the valve block to be moved to the second position, and establishing a fluid passage between the cartridge and the injection needle. The release of the energy stored in the spring may, e.g., be caused by a part moving inside the cassette housing activating a release mechanism.

The waste reservoir may be provided with flexible walls. According to this embodiment, the waste reservoir may be able to expand as waste liquid and/or gas is received in the waste reservoir. The waste reservoir could, e.g., be in the form of a bag.

The waste reservoir may comprise a check valve allowing fluid and/or gas to enter the waste reservoir, via the valve block, while preventing fluid and/or gas from leaving the waste reservoir. According to this embodiment it is efficiently prevented that waste liquid and/or gas leaves the waste reservoir once it has been received therein. Thereby the waste liquid and/or gas is efficiently contained in the waste reservoir, and the risk of waste liquid and/or gas leaking from the cassette is minimised. Furthermore, the risk of accidentally injecting waste liquid and/or gas via the injection needle is also minimised.

The check valve may, e.g., be spring biased. In this case a pressure prevailing in the valve block must be sufficient to overcome the force of the spring acting on the check valve, in order to open the check valve and allow waste liquid and/or gas to enter the waste reservoir via the valve block.

Alternatively or additionally, a hydrophobic membrane may be arranged at an inlet of the waste reservoir. In this case the hydrophobic membrane may be of a kind which expands when it comes into contact with a liquid. When the membrane expands, it blocks the inlet to the waste reservoir, thereby preventing further flow of liquid and/or gas into the waste reservoir. This may be used in the following manner. When an air shot is performed prior to delivery of the medical drug, it may be desirable to direct gas or fumes to the waste reservoir, while preventing that the liquid medical drug is transferred to the waste reservoir, in order to ensure that the entire dose of medical drug is delivered. The valve block may then initially be positioned in the first position, establishing a fluid passage between the cartridge and the waste reservoir. The air shot is then performed, transferring gas to the waste reservoir. As soon as all the gas present in the cartridge and the valve block has been moved to the waste reservoir, liquid drug reaches the hydrophobic membrane. As a consequence the membrane expands and prevents the liquid drug from entering the waste reservoir. This further causes the pressure inside the cartridge to increase, which may be detected e.g. through measuring plunger depression force and/or driving motor current to hence provide an automatic feedback as to when the liquid meet the hydrophobic membrane. The valve block may then be moved to the second position, establishing a fluid passage between the cartridge and the injection needle, and the cassette is ready for delivering the medical drug via the injection needle.

As an alternative, completion of an air shot may be detected in other ways. For instance, a user operating the cassette may visually inspect the interior of the cassette, and when the liquid drug reaches the valve block it is determined, that the air shot has been completed.

As another alternative, a suitable air shot may be ensured in other ways, thereby ensuring a minimal drug waste, while preventing that air is delivered from the cassette. For instance, movements of one or more plungers inside the cartridge may be limited in such a manner that an optimal air shot is obtained.

The cassette may advantageously be held in a position where the injection needle points in an upwards direction during the air shot. Thereby it is ensured that any air contained inside the cassette is not trapped during the air shot, but is instead passed to the waste reservoir.

The disposable cassette may further comprise a sledge arranged inside the cassette housing, said sledge being arranged to cause movements of parts arranged inside the cassette housing in order to cause medical drug to be delivered. The sledge may advantageously be arranged to move along a longitudinal direction defined by the cassette, such as a direction defined by the injection needle and/or the cartridge. The sledge may be mounted in or on guiding rails which restrict the movements of the sledge inside the cassette housing.

The sledge may, e.g., be arranged to cause movements of the injection needle in order to advance the injection needle to protrude out of the cassette housing when drug is to be delivered from the cassette. Alternatively or additionally, the sledge may be arranged to cause movements of one or more plungers arranged inside the cartridge in order to perform air shots and/or deliver medical drug. Alternatively or additionally, the sledge may be arranged to operate the cartridge in order to cause reconstitution of the medical drug prior to delivery of the drug.

The sledge may comprise a locking mechanism which prevents further movements of the sledge when the locking mechanism is in a locking position, e.g. after use of the cassette.

According to this embodiment, once the cassette has been used and the medical drug contained in the cartridge has been delivered, it is no longer possible to move the sledge. This includes further movements in a direction in which the sledge was moved during operation of the cassette, as well as movements in a reverse direction, i.e. a direction which is opposite to the direction in which the sledge was moved during operation of the cassette. Thereby it is prevented that the cassette can be reset to a state where it can be reused, because it is not possible to move the sledge in a manner which causes medical drug contained in the cartridge to be delivered. For instance, the locking mechanism may be used in the following manner. When the delivery of the drug has been completed, the injection needle may be retracted into the cassette housing, and the locking mechanism may be moved to a locking position. The injection needle is then prevented from subsequently being moved out of the cassette housing, and reuse of the cassette is thereby prevented.

The sledge may further be arranged to cause movements of the valve block between the first and second positions. According to this embodiment, the valve block is automatically switched between the first and second positions when the sledge is moved inside the cassette housing in order to cause delivery of the medical drug. As described above, this ensures that the movements of the valve block are synchronized with the steps in the delivery process.

The cartridge may be a dual-chamber cartridge, wherein a dry form of an active ingredient of the drug is stored in a first chamber of the cartridge, and a diluent is stored in a second chamber of the cartridge, and the cartridge may be operable to bring the active ingredient and the diluent into contact in order to mix the active ingredient and the diluent, thereby obtaining a reconstituted drug to be delivered from the cassette. Such dual-chamber cartridges are normally used when the stability of the liquid medical drug is low. In this case the stability of the drug is considerably increased when the drug is stored in a dry form instead of in a liquid form. The active ingredient may, e.g., be in a lyophilized form, or it may be in the form of a powder or a pellet.

According to this embodiment, when it is desired to deliver the medical drug from the cassette, the active ingredient and the diluent must initially be brought together and mixed, thereby reconstituting the medical drug in a liquid form. This may include breaking a seal or establishing a fluid connection between the two chambers of the dual-chamber cartridge. The diluent may be sucked or pushed into the first chamber containing the active ingredient. As an alternative, the active ingredient may be moved into the second chamber containing the diluent. The mixing may include stirring and/or shaking the active ingredient and the diluent when these have been brought together.

In dual-chamber cartridges, a relatively large amount of air or gas is often present in the cartridge when the drug has been reconstituted. It is therefore very important that an air shot is performed after the reconstitution of the medical drug and before the reconstituted drug is delivered. However, the air or gas present in the cartridge may be toxic or otherwise hazardous. In this case it is very important that the air or gas originating from the air shot is contained inside the cassette housing, and that the user operating the cassette is prevented from coming into contact with the air or gas. As described above, according to the invention this is obtained by ensuring that the air shot is transferred to the waste reservoir, which is arranged inside the cassette housing, via the valve block. The cassette according to the first aspect of the invention is, thus, particularly suitable for use with a dual-chamber cartridge.

The disposable cassette may further comprise a removable part, said removable part preventing operation of the cassette when mounted on the cassette, and operation of the cassette may be allowed when the removable part has been removed. The removable part may be completely removable, or it may be partly removable. In the latter case, a portion of the removable part may become detached from the cassette housing, while another portion of the removable part may remain attached to the cassette housing. According to this embodiment, the removable part must be, partly or completely, removed before the cassette can be operated to cause the medical drug to be delivered. This allows a user operating the cassette to easily detect whether or not the cassette has already been used, simply by establishing whether or not the removable part has been removed from the cassette. Thereby the risk of accidentally attempting to use the same cartridge twice is considerably reduced. It is furthermore avoided that a user unintentionally activates a new cassette prior to actually intended, and furthermore the risk of accidentally attempting the use is reduced.

The removable part may, e.g., be in the form of a seal, which ensures that the cassette is properly sealed during storage, and which must be broken before the cassette can be operated to deliver the medical drug.

In the case that the cassette must be mounted in an injector device in order to operate the cassette to cause the medical drug to be delivered, the removable part may prevent the cassette from being mounted in the injector device as long as the removable part is mounted on the cassette.

An absorbent material may be arranged inside the cassette housing in order to contain any spilled liquid inside the cassette housing. According to this embodiment, in the case that liquid is accidentally spilled inside the cartridge, the absorbent material will absorb the liquid, thereby preventing the liquid from leaving the cassette housing, and efficiently containing the liquid inside the cassette housing. Accordingly, the risk of the user operating the cassette coming into contact with toxic or hazardous material is minimised, and it is ensured that such material is properly handled when the cassette is disposed of in a controlled manner after use.

The disposable cassette may further comprise one or more interface parts arranged to engage with interface parts of an injector device, thereby allowing operation of the cassette by means of the injector device. According to this embodiment, the cassette is mounted in a reusable injector device when it is desired to deliver the medical drug. The operation of the cassette and the delivery of the drug are then controlled by means of the injector device. When the delivery of the drug has been completed, the cassette is removed from the injector device and disposed of in a suitable manner. The injector device is then ready to receive another cassette and to deliver the medical drug contained in this cassette. The injector device may, e.g., be in the form of an auto-injector device.

According to a second aspect, the invention provides an injector device comprising:
 a housing defining a cavity arranged to receive a disposable cassette according to the first aspect of the invention, said housing comprising a movable lid allowing a disposable cassette to be inserted into or removed from the cavity,
 valve operating means arranged to operate a valve block of a disposable cassette arranged in the cavity, and
 cartridge operating means arranged to cooperate with a cartridge of a disposable cassette arranged in the cavity in order to cause medical drug to be delivered.

The injector device according to the second aspect of the invention is adapted to hold and cooperate with a disposable cassette according to the first aspect of the invention. The injector device is preferably a reusable injector device. Thus, when it is desirable to deliver a dose of medical drug, a disposable cassette is arranged in the cavity of the injector device, and the cassette is operated, using the injector device, and via the valve operating means and the cartridge operating means, e.g. in the manner described above with reference to the first aspect of the invention. This results in the medical drug contained in the disposable cassette being delivered. Finally, the disposable cassette is removed from the injector device and disposed of in a suitable and safe manner. Then the injector device is ready for receiving a new disposable cassette in order to deliver the medical drug contained therein.

Operating the disposable cassette by means of an injector device, as described above, even further decreases the risk of a user operating the cassette coming into contact with liquid or gas originating from the medical drug contained in the cassette.

The valve operating means may comprise a movable sledge arranged inside the cavity. According to this embodiment, the movable sledge is moved inside the cavity of the injection device during operation of the cassette. The movable sledge then cooperates with the valve block inside the cassette housing in such a manner the movements of the sledge causes the valve block to move between the first and the second positions. The movable sledge may, e.g., be arranged to cooperate with a manipulator arranged on an exterior part of the cassette housing. In this case the valve block is mechanically moved between the first and the second positions by means of the movable sledge, and via the manipulator.

The movable sledge may further be adapted to move an injection needle of a disposable cassette arranged in the cavity between a retracted position and a position in which the injection needle is ready for injection. According to this embodiment the movable sledge controls the operation of the valve block as well as the movement of the injection needle. Thereby the operation of the valve block and the movement of injection needle are synchronised.

The injector device may further comprise a motor for operating the valve operating means and/or the cartridge operating means. This ensures that the medical drug is delivered in a precise manner, e.g. at a substantially constant pace. In this case the injector device may be referred to as an auto-injector.

According to a third aspect the invention provides a method for operating a disposable cassette for storing and delivering a medical drug, the cassette comprising a cartridge containing the medical drug, a waste reservoir, an injection needle or an injection needle mounting interface, and a valve block arranged inside a cassette housing, the method comprising the steps of:

arranging the valve block in a first position establishing a fluid passage between the cartridge and the waste reservoir, while preventing fluid flow from the cartridge to the injection needle or the injection needle mounting interface, operating a plunger of the cartridge to perform an air shot, thereby moving liquid and/or gas from the cartridge to the waste reservoir, and moving the valve block to a second position establishing a fluid passage between the cartridge and the injection needle or the injection needle mounting interface, while preventing fluid flow from the cartridge to the waste reservoir, without a user operating the cassette coming into direct contact with parts arranged inside the cassette housing, thereby preparing the cassette for delivering the medical drug from the cartridge via the injection needle.

It should be noted that a person skilled in the art would readily recognise that any feature described in combination with the first aspect of the invention could also be combined with the second or third aspects of the invention, that any feature described in combination with the second aspect of the invention could also be combined with the first or third aspects of the invention, and that any feature described in combination with the third aspect of the invention could also be combined with the first or second aspects of the invention.

The method according to the third aspect of the invention is very suitable for operating a disposable cassette according to the first aspect of the invention. The disposable cassette is preferably operated in the following manner.

Initially the valve block is positioned in the first position, thereby establishing a fluid passage between the cartridge and the waste reservoir, via the valve block, while preventing a fluid flow from the cartridge to the injection needle. The method may further comprise the step of mounting the injection needle in the cassette.

Then a plunger of the cartridge is operated, thereby pushing liquid and/or gas contained in the cartridge in a direction towards the valve block. Since the valve block is arranged in the first position, this results in liquid and/or gas from the cartridge being transferred to the waste reservoir. Thus, an air shot is performed, and the gas resulting from the air shot is received in the waste reservoir.

When the air shot has been completed, the valve block is moved to the second position, thereby establishing a fluid passage between the cartridge and the injection needle, while preventing a fluid flow from the cartridge to the waste reservoir. This is performed without a user operating the cassette coming into contact with parts arranged inside the cassette housing. As described above with reference to the first aspect of the invention, the risk of a user accidentally coming into contact with the medical drug or fumes of the medical drug stored in the cassette is thereby minimised. Furthermore, the risk of toxic or otherwise hazardous liquid and/or gas leaking from the cassette is also minimised.

When the valve block has been moved to the second position, the cassette is ready for delivering the medical drug, e.g. in the form of an injection. The delivery may be performed by operating the plunger of the cartridge.

The cartridge may be a dual-chamber cartridge, wherein a dry form of an active ingredient of the drug is stored in a first chamber of the cartridge, and a diluent is stored in a second chamber of the cartridge, and the method may further comprise the steps of:

bringing the active ingredient and the diluent into contact, and mixing the active ingredient and the diluent, thereby obtaining a reconstituted drug to be delivered from the cassette.

According to this embodiment, the medical drug is reconstituted prior to the delivery of the drug from the cassette, preferably immediately before the medical drug is delivered from the cassette. This has already been described in detail above with reference to the first aspect of the invention.

The step of moving the valve block may comprise manipulating a manipulating mechanism arranged on an exterior part of the cassette housing, said manipulating mechanism being connected to the valve block. As an alternative, the step of moving the valve block may be performed automatically as a consequence of moving other parts arranged inside the cassette housing, during the steps of preparing the cassette for injection of the medical drug. This has also been described in detail above with reference to the first aspect of the invention.

BRIEF DESCRIPTION OF THE DRAWINGS

The invention will now be described in further detail with reference to the accompanying drawings in which.

DETAILED DESCRIPTION OF THE DRAWINGS

Figure 1:
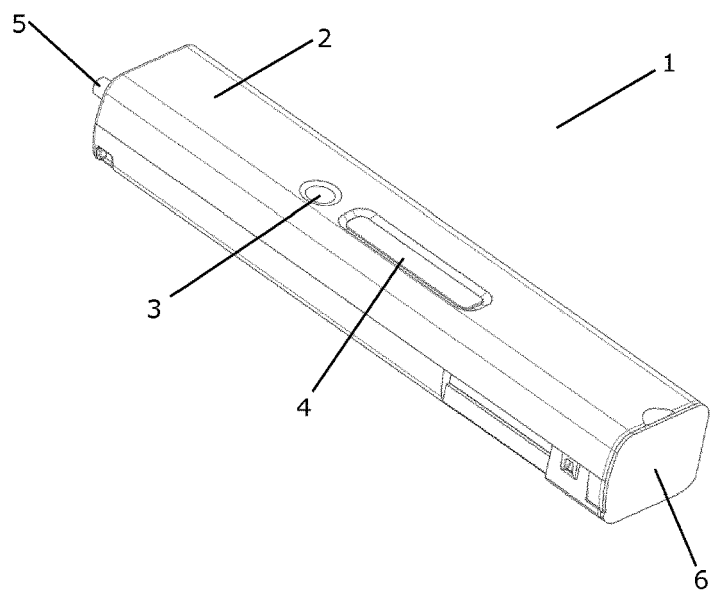
FIGS. 1-3 are perspective views of a disposable cassette according to an embodiment of the invention.
Figure 2:
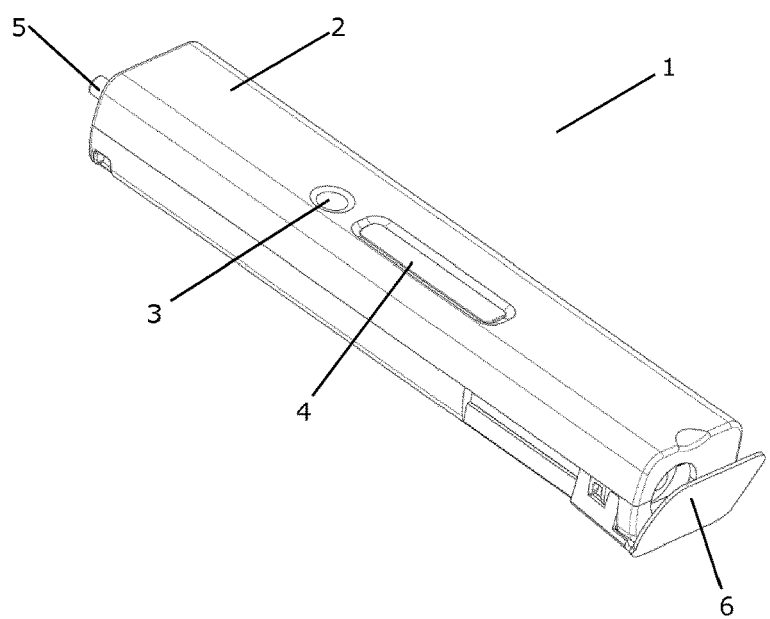
Figure 3:
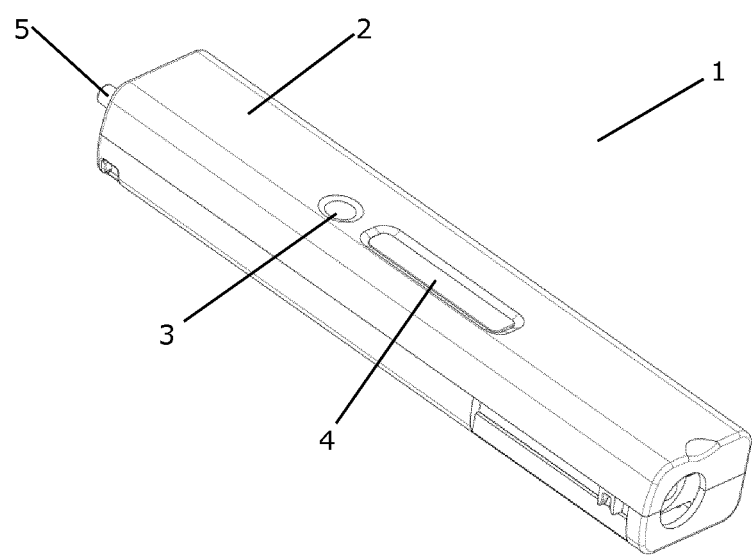

FIGS. 1-3 are perspective views of a disposable cassette 1 according to an embodiment of the invention. The cassette 1 comprises a cassette housing 2 enclosing a number of parts arranged inside the cassette housing 2. The cassette 1 is capable of storing and delivering medical drug contained inside the cassette housing 2.

The cassette housing 2 is provided with a first window 3 allowing a user operating the cassette 1 to visually inspect the performance of an air shot. This will be described in further detail below with reference to FIGS. 4-10.

The cassette housing 2 is further provided with a second window 4 allowing a user operating the cassette 1 to visually inspect a medical drug stored in the cassette 1. This will also be described in further detail below with reference to FIGS. 4-10.

A needle cap 5 protrudes from the cassette housing 2. The needle cap 5 covers an injection needle arranged inside the cassette housing 2, and must be manually removed before the cassette 1 can be operated to deliver a dose of medical drug.

A removable seal 6 is mounted at one end of the cassette housing 2. The seal 6 must be removed before it is possible to operate the cassette 1 in such a manner that medical drug stored in the cassette 1 is delivered. Once the seal 6 has been removed it is not possible to remount it on the cassette housing 2. Thereby it can easily be detected whether or not a cassette 1 has already been used. If the seal 6 is still mounted on the cassette housing 2, then the cassette 1 is intact and has not yet been used. Accordingly, the full dose of medical drug is still contained in the cassette 1. On the other hand, if the seal 6 has been removed, the cassette 1 has most likely already been used, i.e. the medical drug has probably already been partly or fully delivered. In any event, the sealing of the cassette housing 2 has been broken, and it may therefore not be safe to use cassette 1, even if some or all of the medical drug is still present in the cassette 1. Furthermore, if the medical drug has previously been partly delivered, the remaining dose is uncertain. Thus, in the case that the seal 6 has been removed from the cassette housing 2, it should not be attempted to use the cassette 1, and the cassette 1 should instead be disposed of in a suitable manner.

In FIG. 1 the seal 6 is still mounted on the cassette housing 2, in FIG. 2 the seal 6 is being removed, and in FIG. 3 the seal has been removed.

FIGS. 4-10 illustrate the disposable cassette 1 of FIGS. 1-3 in various positions during a process of delivering medical drug from the cassette 1. A part of the cassette housing 2 has been removed in order to reveal various parts arranged inside the cassette housing 2.

The cassette 1 comprises a cartridge 7, a waste reservoir 8 arranged to receive waste liquid and/or gas, an injection needle 9 and a valve block 10, all arranged inside the cassette housing 2.

The cartridge 7 is in the form of a dual-chamber cartridge, i.e. it comprises a first chamber 11 containing a dry form of an active ingredient of the medical drug, and a second chamber 12 containing a diluent.

The waste reservoir 8 is provided with flexible walls, allowing the waste reservoir 8 to expand when it receives waste liquid and/or gas.

Figure 4:
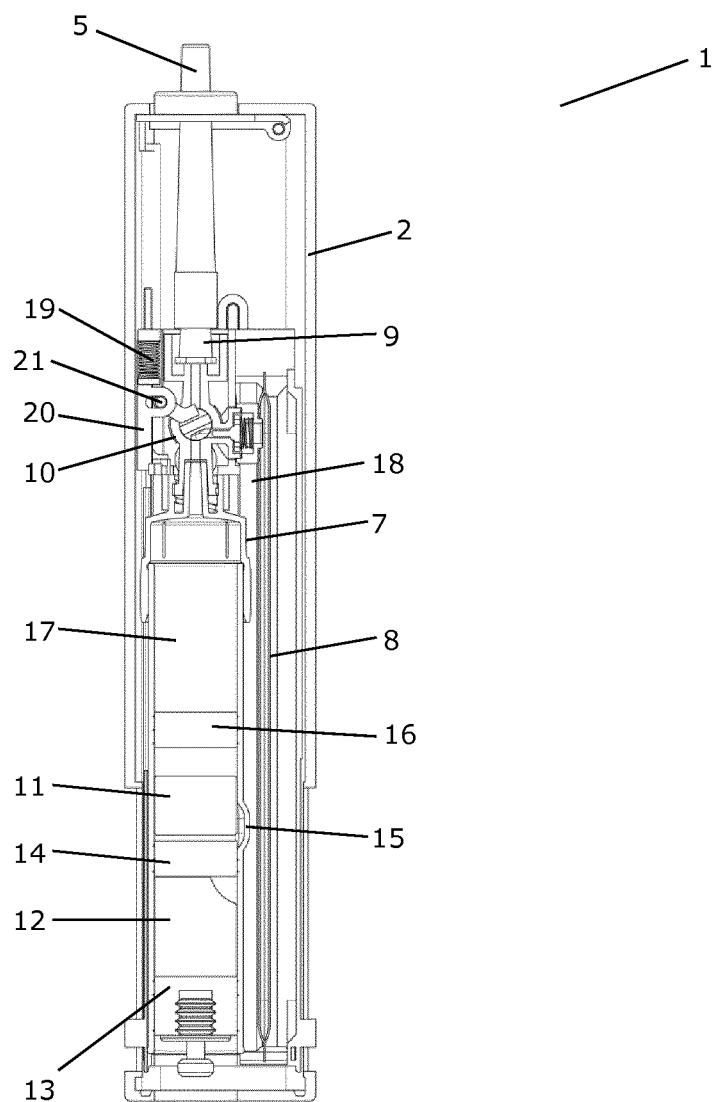
FIGS. 4-10 illustrate the disposable cassette of FIGS. 1-3 in various positions during a delivery process.
Figure 5:
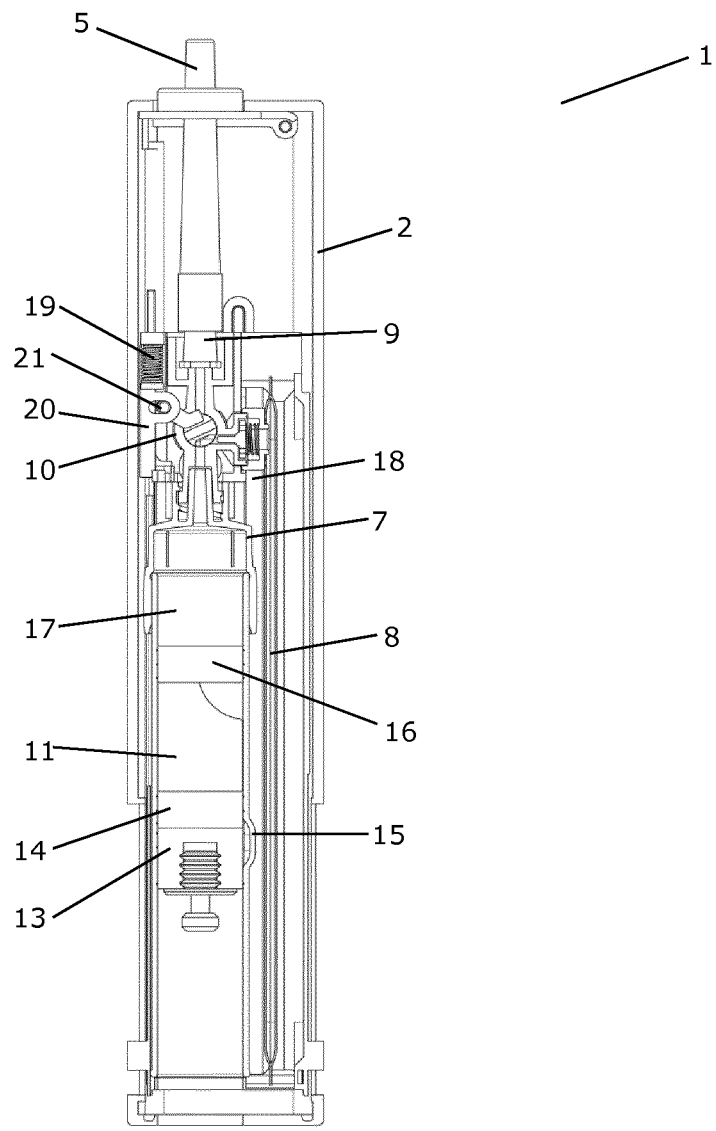

In FIGS. 4 and 5 the injection needle 9 is covered by the needle cap 5, and in FIGS. 6-10 the needle cap 5 has been removed, thereby exposing the tip of the injection needle 9.

The valve block 10 is movable between a first position and a second position. In the first position, the valve block 10 establishes a fluid passage between the cartridge 7 and the waste reservoir 8, while preventing fluid flow from the cartridge 7 to the injection needle 9. In the second position the valve block 10 establishes a fluid passage between the cartridge 7 and the injection needle 9, while preventing fluid flow from the cartridge 7 to the waste reservoir 8.

The operation of the disposable cassette 1 will now be described with reference to FIGS. 4-10.

In FIG. 4 the cassette 1 is shown in a position which may be applied during storage of the cassette 1. The injection needle 9 is covered by the needle cap 5. The first chamber 11 and the second chamber 12 of the cartridge 7 are sealed with respect to each other, thereby ensuring that the active ingredient in dry form is kept separate from the diluent. The valve block 10 is in the first position, i.e. a fluid passage is established between the cartridge 7 and the waste reservoir 8.

When it is desirable to deliver medical drug from the cassette 1, a first plunger 13 is pushed in a direction towards the injection needle 9. Since the liquid diluent contained in the second chamber 12 is incompressible, this will cause a second plunger 14 to be moved in the direction towards the injection needle 9, until it reaches a position where a recess 15 is formed in the wall of the cartridge 7. The liquid diluent can then pass into the first chamber 11, via the recess 15, and thereby the active ingredient of the medical drug and the liquid diluent are brought together in the first chamber 11. Furthermore, a third plunger 16 is moved in the direction towards the injection needle 9 by the liquid diluent entering the first chamber 11. Thereby air contained in a third chamber 17 is displaced out of the cartridge 7. Since the valve block 10 is in the first position, the air is transferred to the waste reservoir 8, via the valve block 10. Accordingly, this waste air is collected in the waste reservoir 8, and there is no risk that it is delivered via the injection needle 9, or otherwise leaking from the cassette housing 2. Accordingly, the waste air from the third chamber 17 of the cartridge 7 is safely contained within the cassette housing 2.

When the first plunger 13 has been moved into abutment with the second plunger 14, and all of the diluent has passed into the first chamber 11, the first plunger 13 moves the second plunger 14 slightly in the direction towards the injection needle 9, thereby closing the passage formed by the recess 15. This is the position illustrated in FIG. 5.

Thus, in FIG. 5 the active ingredient of the medical drug and the liquid diluent have been brought together in the first chamber 11 of the cartridge 7, and reconstitution of the medical drug can take place in the first chamber 11. This may include shaking and/or turning the cassette 1 in order to ensure that the drug is properly mixed. The reconstitution of the medical drug can be visually inspected via the second window (4 in FIGS. 1-3) formed in the cassette housing 2.

Figure 6:
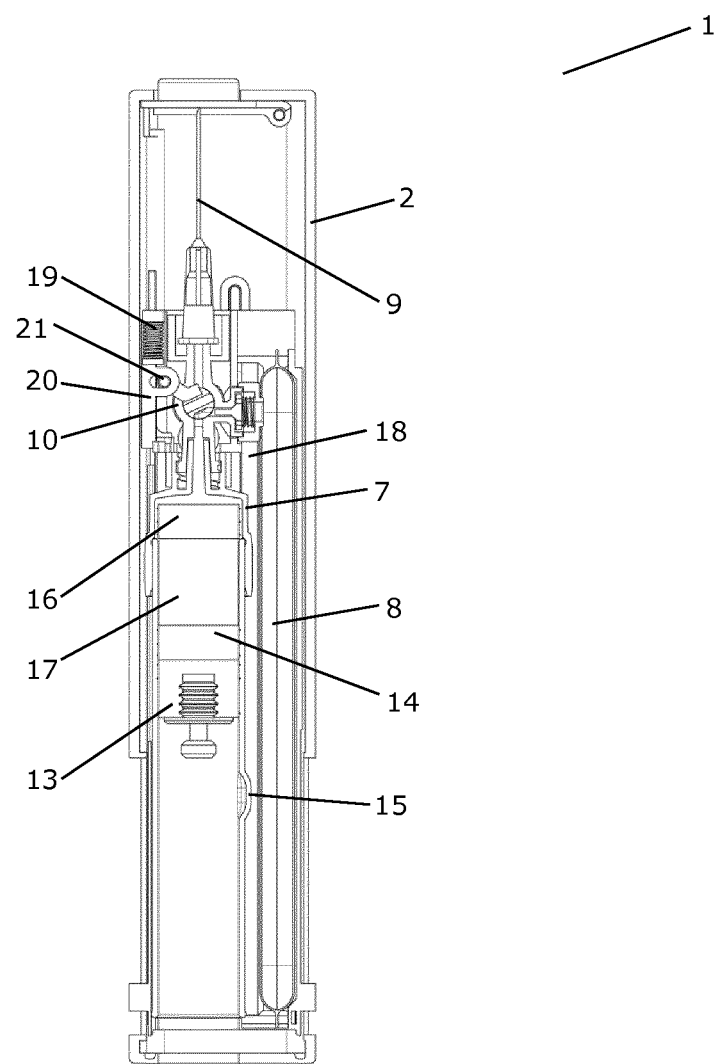

When the drug has been reconstituted, an air shot must be performed. To this end, the first plunger 13 is moved further in the direction towards the injection needle 9, thereby causing the third plunger 16 to move to an end position, as shown in FIG. 6. This causes the rest of the air contained in the third chamber 17 to be passed to the waste reservoir 8, via the valve block 10. During the air shot, the cassette 1 may advantageously be held in a position where the injection needle 9 points in an upwards direction, in order to prevent air from being trapped in the system, and in order to ensure that the air is instead passed to the waste reservoir 8.

Furthermore, the reconstituted drug is allowed to flow past the third plunger 16 and into the valve block 10, thereby displacing any air present in the cartridge 7 and the valve block 10 into the waste reservoir 8, i.e. performing an air shot. The air shot can be visually inspected via the first window (3 in FIGS. 1-3) formed in the cassette housing 2. When reconstituted drug reaches an inlet opening of the waste reservoir 8, the air shot has been completed, and the cassette 1 is ready for delivering the reconstituted medical drug. As an alternative, it may be concluded that the air shot has been completed when it can be visually confirmed that the reconstituted, liquid drug has reached the valve block 10.

In FIG. 6 the flexible walls of the waste reservoir 8 have been expanded, due to the air, and possibly liquid, received in the waste reservoir 8 during the reconstitution process and the air shot. Furthermore, the needle cap 5 has been removed from the injection needle 9, thereby exposing the tip of the injection needle 9. However, the injection needle 9 is still completely accommodated inside the cassette housing 2.

In order to advance the tip of the injection needle 9 out of the cassette housing 2, a sledge 18 carrying the cartridge 7, the waste reservoir 8, the injection needle 9 and the valve block 10 is moved in the direction towards the injection needle 9. When this movement of the sledge 18 is commenced, a locking mechanism (not visible) releases energy stored in a compressible spring 19. The released energy pushes a slider 20 in a reverse direction, i.e. in a direction away from the injection needle 9. The slider 20 is connected to the valve block 10 via a pin 21. Thereby the reversal movement of the slider 20 causes the valve block 10 to be moved into the second position. This is the position illustrated in FIG. 7.

Figure 7:
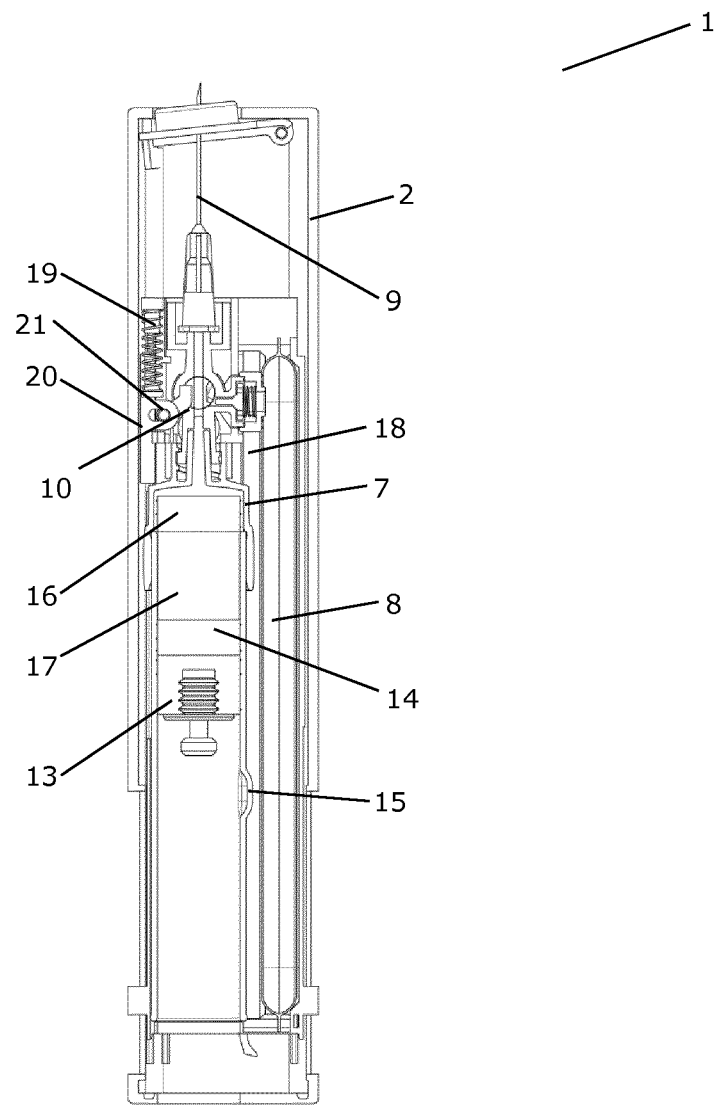

Thus, in FIG. 7 the injection needle 9 has been moved in such a manner that the tip of the injection needle 9 protrudes from the cassette housing 2. Furthermore, it can be seen that the compressible spring 19 is in a released state, and that the valve block 10 is in the second position, i.e. the valve block 10 establishes a fluid passage between the cartridge 7 and the injection needle 9.

Figure 8:
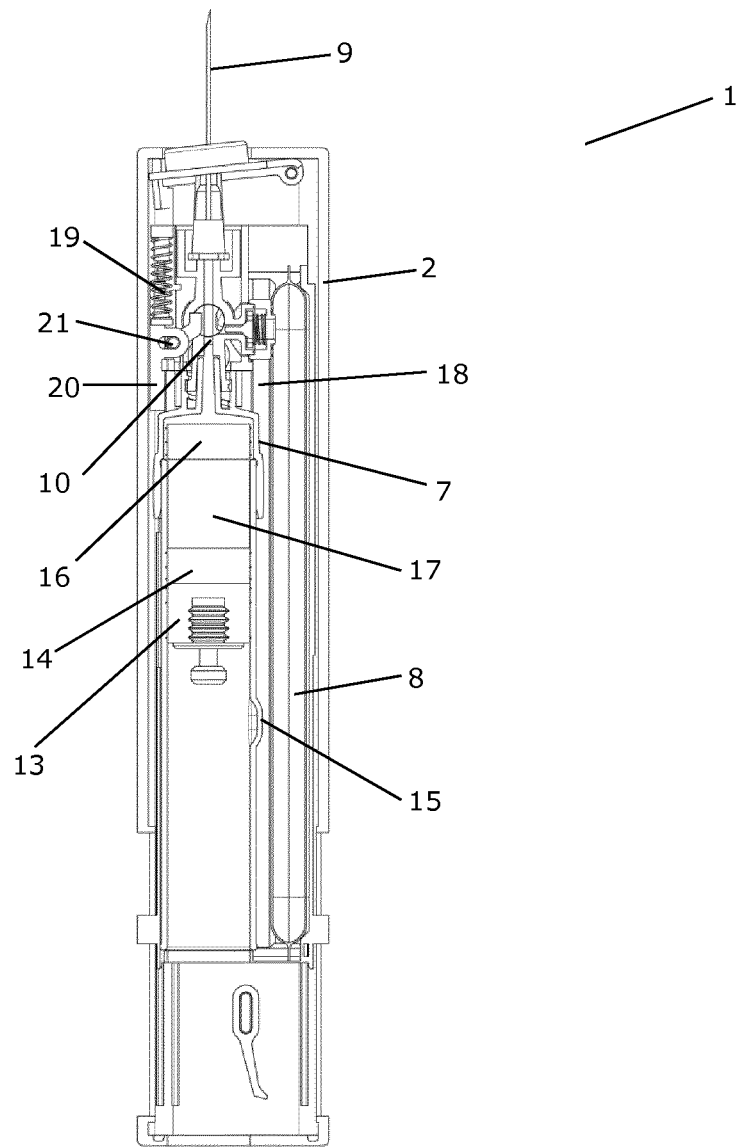

The sledge 18 is then moved further forwards in order to move the injection needle 9 further out of the cassette housing 2, i.e. to the position illustrated in FIG. 8.

Figure 9:
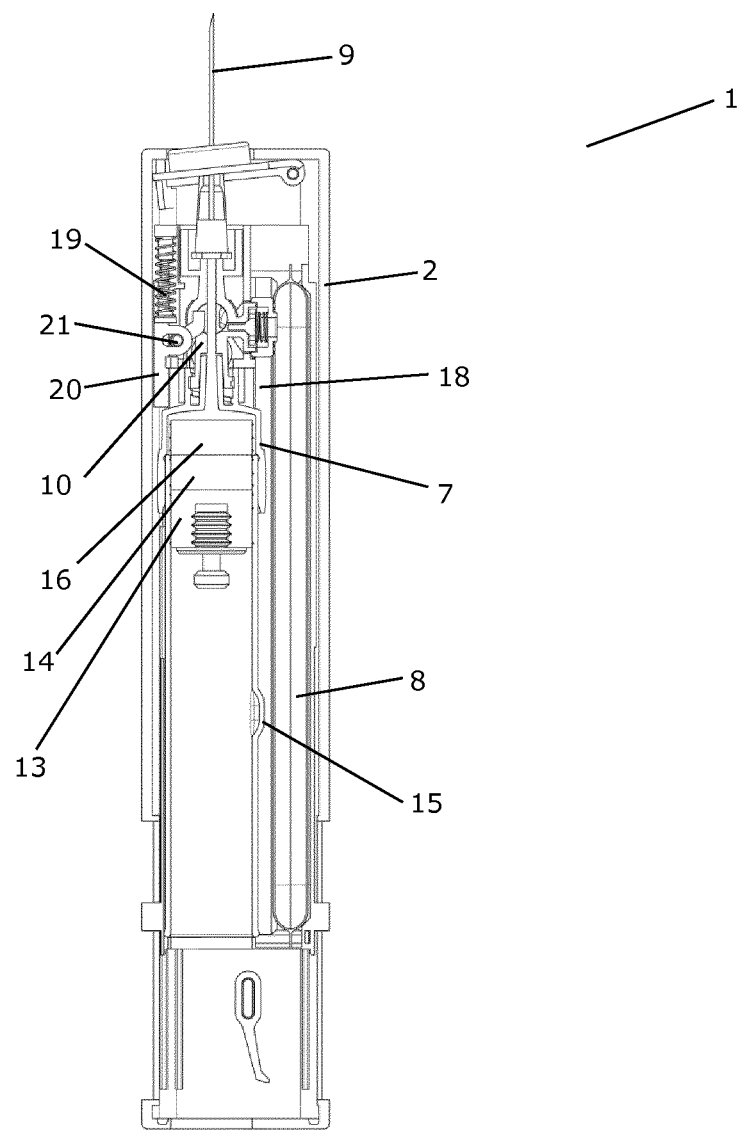

The first plunger 13 is then once again moved in the direction towards the injection needle 9. This causes the reconstituted drug to be transferred out of the first chamber 11 towards the valve block 10. Since the valve block 10 is in the second position, the reconstituted drug is thereby delivered from the injection needle 9, via the valve block 10. FIG. 9 shows the cassette 1 in the position where the entire dose of medical drug has been delivered via the injection needle 9 in this manner.

Figure 10:
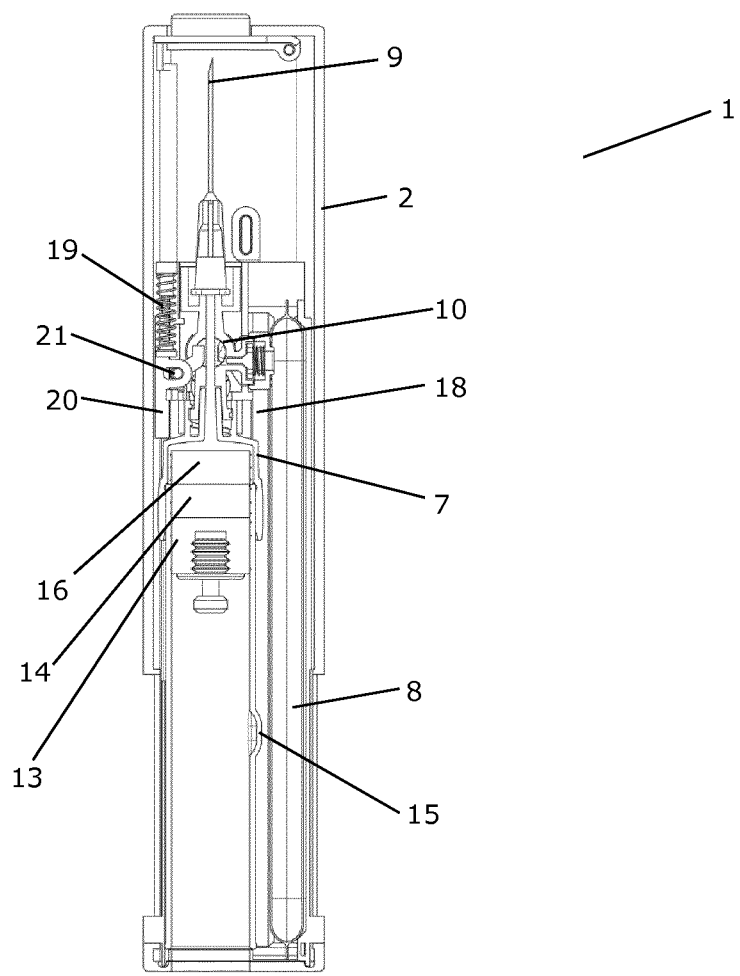

When the delivery of the medical drug has been completed in the manner described above, the sledge 18 is moved in a reverse direction, i.e. in a direction which moves the injection needle 9 back into the cassette housing 2. FIG. 10 shows the cassette 1 in the position where the injection needle 9 has been fully retracted into the cassette housing 2. Thereby the cassette 1 can be safely transported to a location where it can be destructed in a responsible and secure manner, along with the gas and liquid contained in the waste reservoir 8, any residue medical drug remaining in the cartridge 7, the valve block 10 and the injection needle 9, and any spilled medical drug contained inside the cassette housing 2.

Figure 11:
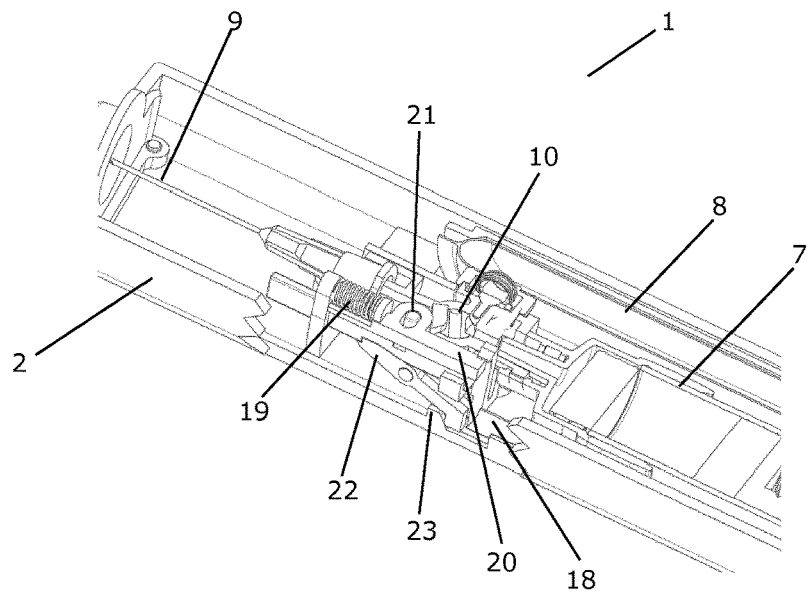
FIGS. 11-13 are perspective views of details of the disposable cassette of FIGS. 1-10, with parts broken away to illustrate a locking mechanism.
Figure 12:
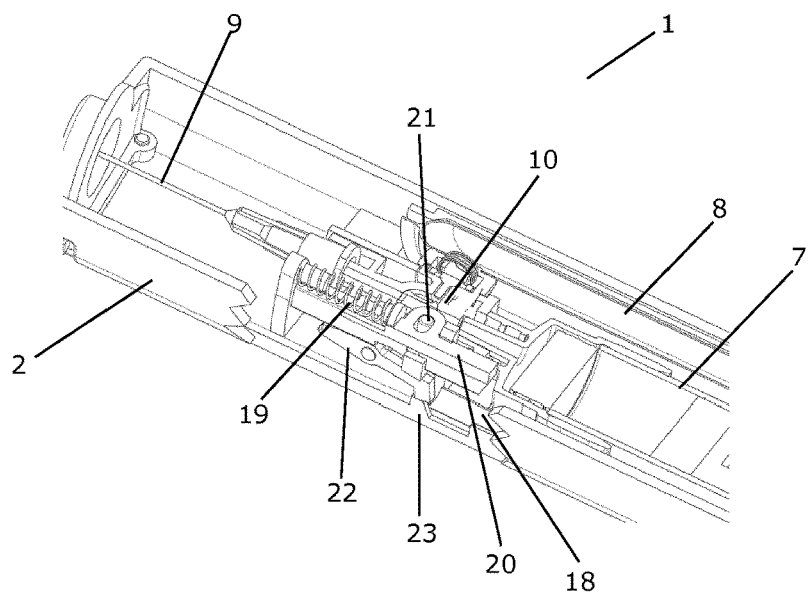
Figure 13:
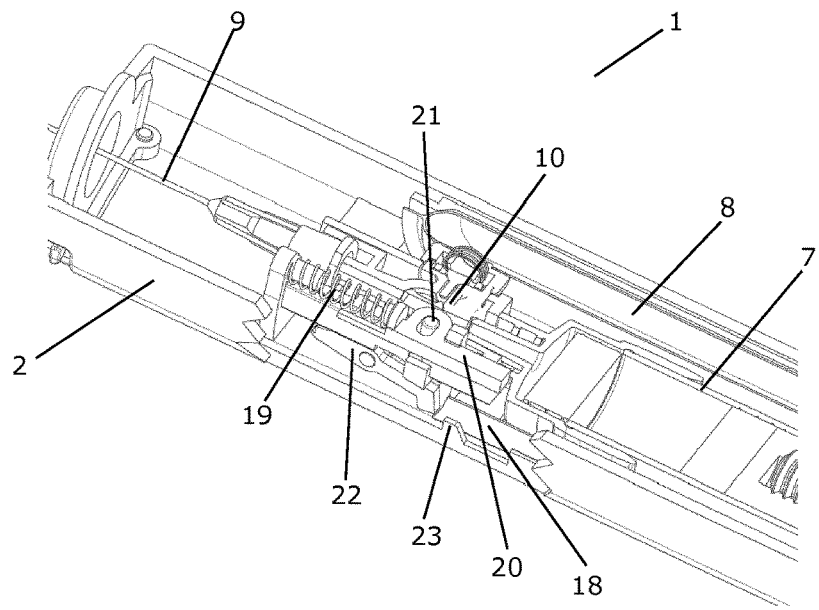

FIGS. 11-13 are perspective views of details of the disposable cassette 1 of FIGS. 1-10. Parts of the cassette housing 2 have been broken away in order to reveal a locking mechanism comprising a locking arm 22 and a cam 23 arranged in the interior of the cassette housing 2.

In FIG. 11 the cassette 1 is in the position illustrated in FIG. 6. Thus, the medical drug has been reconstituted and an air shot has been performed, but the sledge 18 has not yet been moved forward in order to advance the injection needle 9 out of the cassette housing 2. Furthermore, the compressible spring 19 is in a compressed state, and the slider 20 is kept in a position, where it retains the spring 19, by means of the locking arm 23. The locking arm 23 is kept in this locking position by the cam 23.

In FIG. 12 the cassette 1 is in a position which is between the position illustrated in FIG. 6 and the position illustrated in FIG. 7. Thus, the sledge 18 has been moved slightly forward in order to advance the injection needle 9 out of the cassette housing 2. Thereby the sledge 18 has pushed the locking arm 22 out of engagement with the cam 23, and the locking arm 22 has been moved out of the locking position, i.e. the locking arm 23 no longer keeps the slider 20 in the position where it retains the spring 19. As a consequence, the energy stored in the spring 19 has been released, and has pushed the slider 20 is a backwards direction, i.e. in a direction towards the cartridge 7.

The slider 20 is arranged in engagement with the pivot 21 formed on the valve block 10. Therefore the backwards movement of the slider 20 has caused the valve block 10 to be rotated, thereby moving the valve block 10 into the second position, where a fluid passage is established between the cartridge 7 and the injection needle 9.

In FIG. 13 the cassette 1 is in the position illustrated in FIG. 7. Thus, the sledge 18 has been moved further in the forwards direction, and the locking arm 22 has been moved further away from the cam 23. Thereby the locking arm 22 has been moved into a position, where the cam 23 prevents it from being moved back to the position illustrated in FIG. 11. Thereby accidental reuse of the cassette 1 is efficiently prevented.

Figure 14:
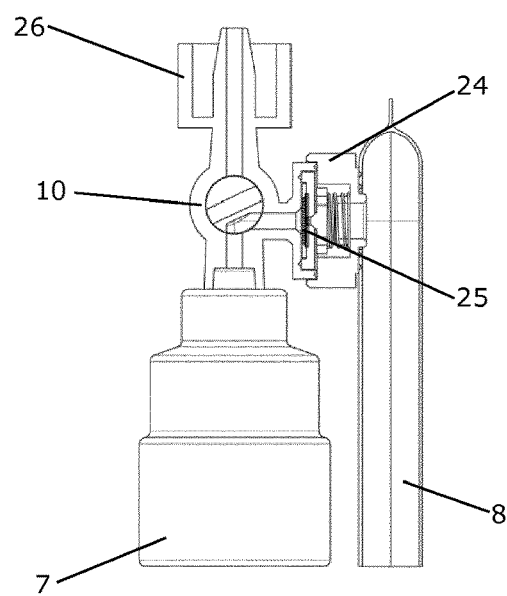
FIGS. 14 and 15 are cross sectional views of a valve block for a disposable cassette according to an embodiment of the invention.
Figure 15:
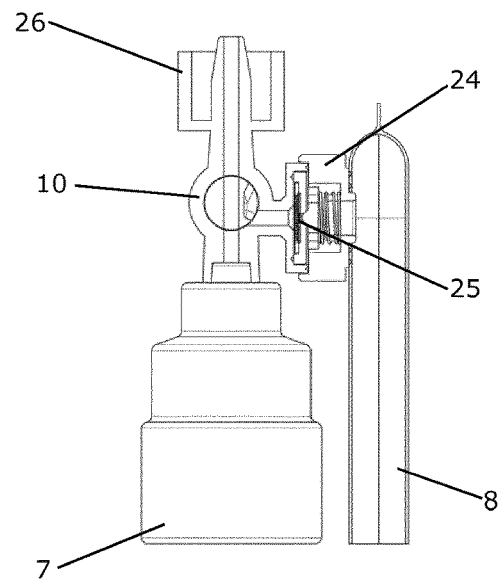

FIGS. 14 and 15 are cross sectional views of a valve block 10 for a disposable cassette 1 according to an embodiment of the invention. A cartridge 7 and a waste reservoir 8 are connected to the valve block 10. The waste reservoir 8 is connected to the valve block 10 via a check valve 24. A hydrophobic membrane 25 is arranged adjacent to the check valve 24. When the hydrophobic membrane 25 comes into contact with a liquid, it expands and thereby blocks the fluid passage to the waste reservoir 8. Thus, this passage will automatically be blocked when an air shot has been completed, and reconstituted drug in liquid form reaches the valve block 10.

In FIG. 14 the valve block 10 is in the first position, i.e. it establishes a fluid passage between the cartridge 7 and the waste reservoir 8. In FIG. 15 the valve block 10 is in the second position, i.e. it establishes a fluid passage between the cartridge 7 and an injection needle which can be mounted at connector 26.

Figure 16:
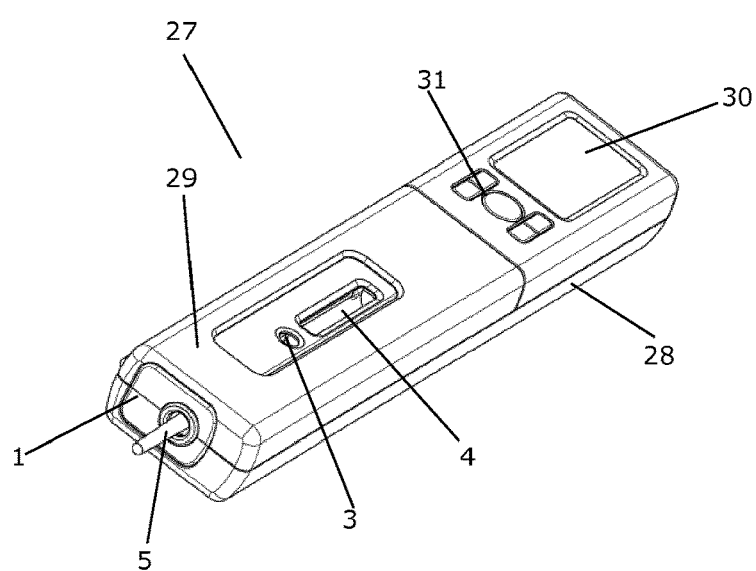
FIGS. 16-18 are perspective views of an injector device according to an embodiment of the invention.
Figure 17:
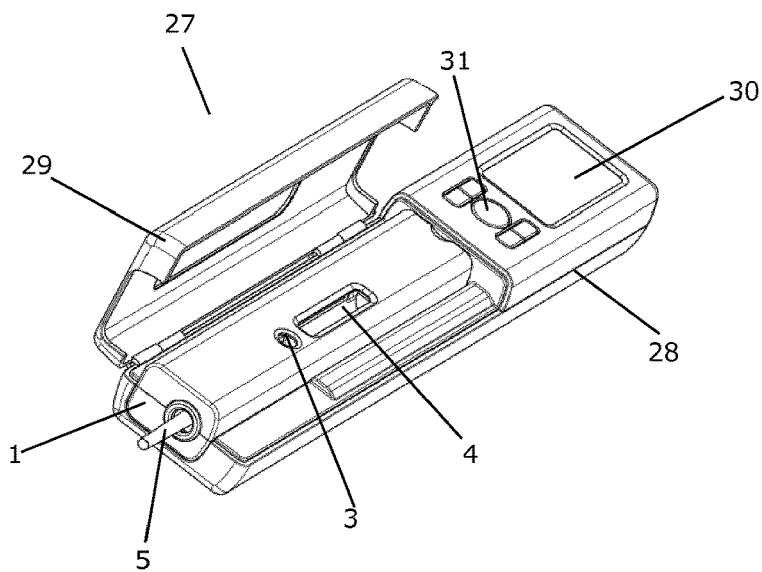
Figure 18:
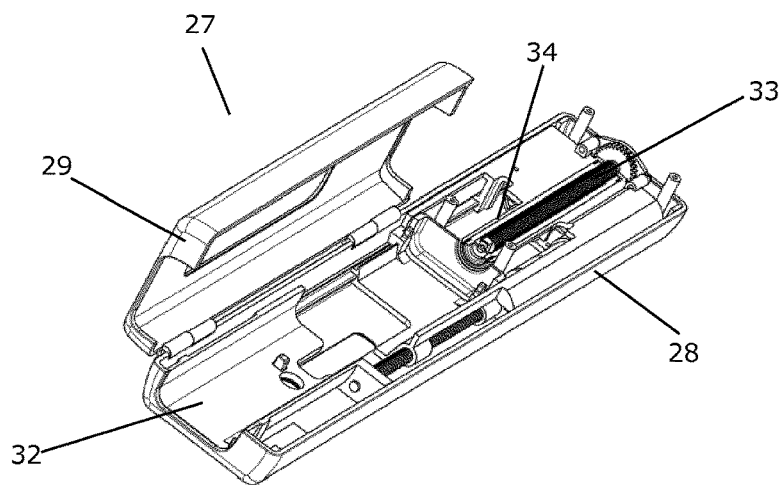

FIGS. 16-18 are perspective views of an injector device 27 according to an embodiment of the invention. The injector device 27 comprises a housing 28 with a lid 29 which allows access to the interior of the housing 28. A disposable cassette 1, such as the cassette illustrated in any of FIGS. 1-13, can be received in the injector device 27. When a disposable cassette 1 is mounted in the injector device 27, the cassette 1 can be operated by means of the injector device 27 in order to deliver medical drug contained in the cassette 1. After delivery of the medical drug, the cassette 1 can be removed from the injector device 27 and disposed of in a suitable manner.

In FIG. 16 the lid 29 is closed, and a cassette 1 is mounted in the injector device 27. The cassette 1 is visible, and the needle cap 5 protrudes from the housing 28. A display 30 and operating buttons 31 are mounted on the housing 28. The operating buttons 31 are used by a user for controlling operation of the cassette 1. The display 30 provides information to the user regarding the progress of the delivery process.

In FIG. 17 the lid 29 is open, and it is illustrated how the cassette 1 is received inside the housing 28.

In FIG. 18 no cassette is mounted in the interior of the housing 28. Furthermore, the part of the housing 28 carrying the display and the operating buttons has been removed in order to reveal parts of the injector device 27 arranged inside the housing 28.

A movable sledge 32 is arranged to cooperate with a manipulator mechanism arranged on an exterior part of the cassette housing of a cassette mounted in the injector device 27, in order to manipulate the valve block of the cassette. Thus, movements of the movable sledge 32 will result in appropriate movements of the valve block of a cassette mounted in the interior of the housing 28. For instance, the movable sledge 32 may cooperate with a sledge arranged inside the cassette housing for causing movements of the injection needle, as described above with reference to FIGS. 4-13.

A lead screw 33 is arranged for causing movements of a plunger activator 34. When a cassette is arranged in the interior of the housing 28, the plunger activator 34 is arranged in abutment with the plunger of the cartridge of the cassette. Thus, the plunger of the cassette can be operated by means of the injector device 27, via the plunger activator 34, and by operating the lead screw 33.

The invention claimed is:

1. An injector device comprising:
   a housing defining a cavity having a disposable cassette arranged therein, said housing comprising a movable lid allowing the disposable cassette to be inserted into or removed from the cavity,
   a movable sledge configured to operate a valve block of the disposable cassette arranged in the cavity, and
   a plunger activator arranged in abutment with a plunger of a cartridge of the disposable cassette arranged in the cavity, the plunger activator being configured to operate the plunger in order to cause a medical drug to be delivered,
   wherein the disposable cassette comprises:
      the cartridge containing the medical drug,
      a waste reservoir arranged to receive waste liquid and/or gas,
      an injection needle or an injection needle mounting interface for mounting an injection needle arranged to deliver the medical drug, and
      the valve block being movable between a first position and a second position, the first position establishing a fluid passage between the cartridge and the waste reservoir, while preventing fluid flow from the cartridge to the injection needle or the injection needle mounting interface, and the second position establishing a fluid passage between the cartridge and the injection needle or the injection needle mounting interface, while preventing fluid flow from the cartridge to the waste reservoir,
      wherein the cartridge, the waste reservoir, the valve block and at least part of the injection needle or the injection needle mounting interface are arranged inside a cassette housing of the disposable cassette, and wherein the valve block is operable to be moved between the first position and the second position without a user operating the disposable cassette coming into direct contact with parts arranged inside the cassette housing.

2. The injector device according to claim 1, wherein movable sledge is arranged inside the cavity.

3. The injector device according to claim 2, wherein the disposable cassette comprises the injection needle, and the movable sledge is further configured to move the injection needle of the disposable cassette arranged in the cavity between a retracted position and a position in which the injection needle is ready for injection.

4. The injector device according to claim 1, further comprising a motor for operating the movable sledge and/or the plunger activator.

5. The injector device according to claim 1, wherein the valve block is operable to be moved between the first position and the second position without a need to open or enter the cassette housing.

6. The injector device according to claim 1, wherein the disposable cassette further comprises a sledge, the sledge being connected to the valve block via a slider and a pin, where movement of the movable sledge moves the sledge which causes the slider and the pin to move the valve block between the first position and the second position.

7. The injector device according to claim 1, wherein the valve block is arranged to be automatically moved between the first position and the second position during operation of the disposable cassette in order to cause the medical drug to be delivered.

8. The injector device according to claim 7, wherein the valve block comprises a compressible spring, and wherein the valve block is moved from the first position to the second position when energy stored in the compressible spring is released.

9. The injector device according to claim 1, wherein the waste reservoir is provided with flexible walls.

10. The injector device according to claim 1, wherein the waste reservoir comprises a check valve allowing fluid and/or gas to enter the waste reservoir, via the valve block, while preventing fluid and/or gas from leaving the waste reservoir.

11. The injector device according to claim 1, wherein the cartridge is a dual-chamber cartridge, wherein a dry form of an active ingredient of the medical drug is stored in a first chamber of the dual-chamber cartridge, and a diluent is stored in a second chamber of the dual-chamber cartridge, and wherein the dual-chamber cartridge is operable to bring the active ingredient and the diluent into contact in order to mix the active ingredient and the diluent, thereby obtaining a reconstituted medical drug to be delivered from the disposable cassette.

12. The injector device according to claim 1, wherein an absorbent material is arranged inside the cassette housing in order to contain any spilled liquid inside the cassette housing.

13. A method for operating an injector device comprising a housing with a movable lid, the housing defining a cavity having a disposable cassette arranged therein for storing and delivering a medical drug, the disposable cassette comprising a cartridge containing the medical drug, a waste reservoir, an injection needle or an injection needle mounting interface, and a valve block arranged inside a cassette housing of the disposable cassette, the injector device further comprising a movable sledge and a plunger activator, the method comprising the steps of:
   arranging the valve block in a first position establishing a fluid passage between the cartridge and the waste reservoir, while preventing fluid flow from the cartridge to the injection needle or the injection needle mounting interface,
   operating a plunger of the cartridge to perform an air shot, thereby moving liquid and/or gas from the cartridge to the waste reservoir, and
   moving the valve block to a second position establishing a fluid passage between the cartridge and the injection needle or the injection needle mounting interface, while preventing fluid flow from the cartridge to the waste reservoir, without a user operating the disposable cassette coming into direct contact with parts arranged inside the cassette housing, thereby preparing the disposable cassette for delivering the medical drug from the cartridge via the injection needle or the injection needle mounting interface.

14. The method according to claim 13, the cartridge being a dual-chamber cartridge, wherein a dry form of an active ingredient of the medical drug is stored in a first chamber of the dual-chamber cartridge, and a diluent is stored in a second chamber of the dual-chamber cartridge, the method further comprising the steps of:

bringing the active ingredient and the diluent into contact, and mixing the active ingredient and the diluent, thereby obtaining a reconstituted medical drug to be delivered from the disposable cassette.

15. The method according to claim 13, wherein the step of moving the valve block comprises manipulating a sledge said sledge being connected to the valve block via a slider and a pin.

* * * * *